United States Patent
Mueller

(10) Patent No.: US 9,402,588 B2
(45) Date of Patent: Aug. 2, 2016

(54) ROTATING UNIT OF A MEDICAL IMAGING DEVICE WITH A HYDROSTATIC SLIDE BEARING AND AN INTEGRATED COOLANT CONDUIT

(71) Applicant: Siemens Aktiengesellschaft, Munich (DE)

(72) Inventor: Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 179 days.

(21) Appl. No.: 14/455,086

(22) Filed: Aug. 8, 2014

(65) Prior Publication Data

US 2015/0043706 A1    Feb. 12, 2015

(30) Foreign Application Priority Data

Aug. 9, 2013  (DE) .......................... 10 2013 215 801

(51) Int. Cl.
*A61B 6/00*    (2006.01)
*A61B 6/03*    (2006.01)

(52) U.S. Cl.
CPC ............... *A61B 6/035* (2013.01); *A61B 6/4452* (2013.01); *A61B 6/4488* (2013.01)

(58) Field of Classification Search
CPC ....... A61B 6/35; A61B 6/4452; A61B 6/4488
USPC ............... 378/4–20, 131, 132, 133, 193–197, 378/199, 200
See application file for complete search history.

(56) References Cited

U.S. PATENT DOCUMENTS

| | | | |
|---|---|---|---|
| 6,404,845 B1 * | 6/2002 | Sharpless ............... | A61B 6/035 378/15 |
| 7,014,361 B1 * | 3/2006 | Ein-Gal ............... | A61N 5/1081 378/197 |
| 2010/0034492 A1 | 2/2010 | Krumme | |

FOREIGN PATENT DOCUMENTS

DE        38 19 390 A1   12/1989

* cited by examiner

*Primary Examiner* — Courtney Thomas
(74) *Attorney, Agent, or Firm* — Steven H. Noll

(57) ABSTRACT

A rotating unit of a medical imaging device has a hydrostatic slide bearing and an integrated coolant conduit. The rotating unit includes at least one stator, at least one rotor that is borne such that it can rotate relative to the stator, and at least one portion of a circulation system for the circulation of a bearing medium, so the rotor is borne hydrostatically floating by the bearing medium. The at least one portion of the circulation system for the circulation of the bearing medium also has at least one stator-side opening and one rotor-side opening to the hydrostatic slide bearing. The rotating unit additionally has at least one at least single-channel rotary joint mounted between the rotor and the stator. The rotating unit is designed such that the bearing medium can be supplied through the stator-side opening into the hydrostatic slide bearing and the bearing medium can be supplied again through the rotor-side opening and the rotary joint into the circulation system again.

20 Claims, 3 Drawing Sheets

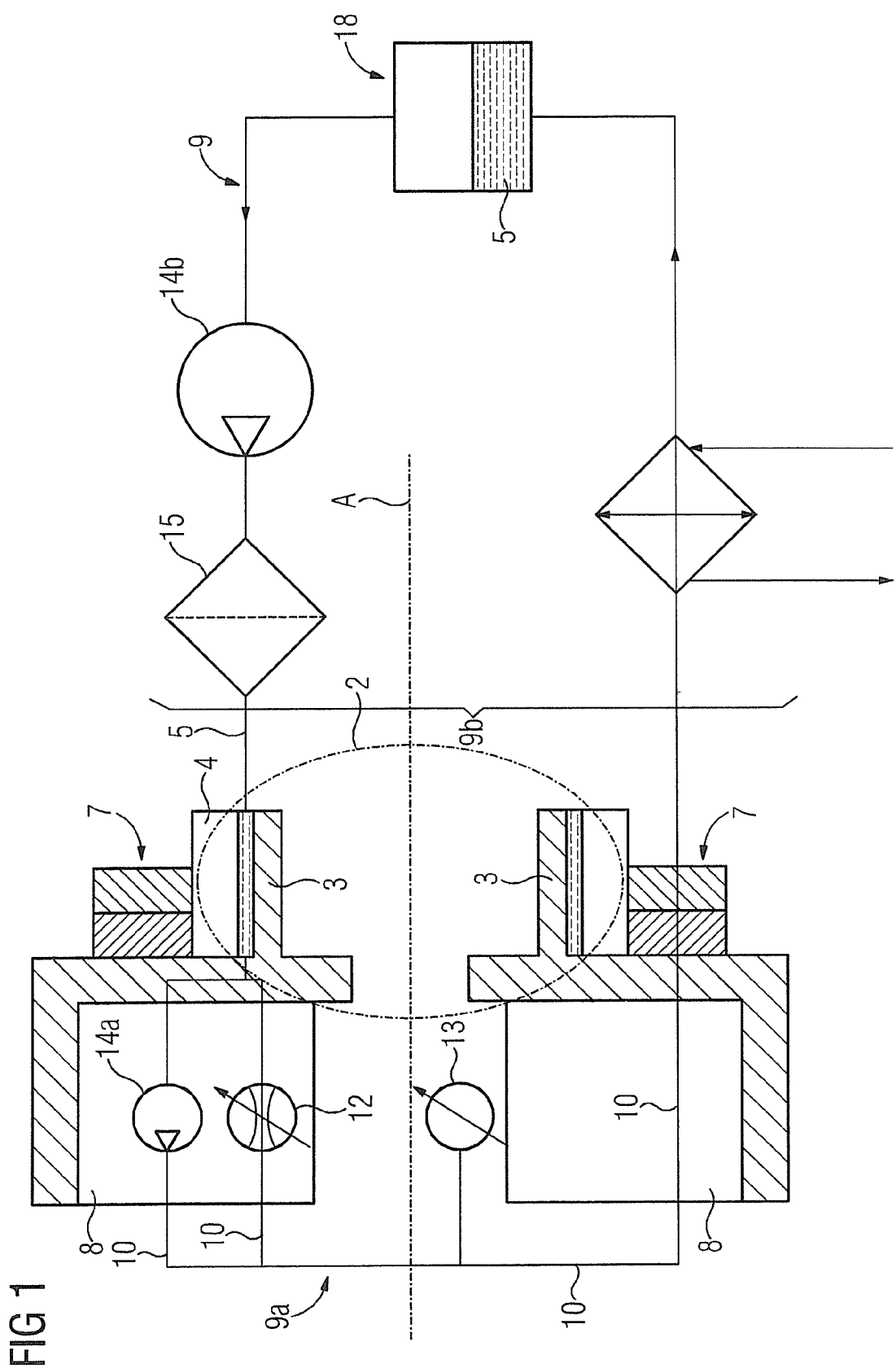

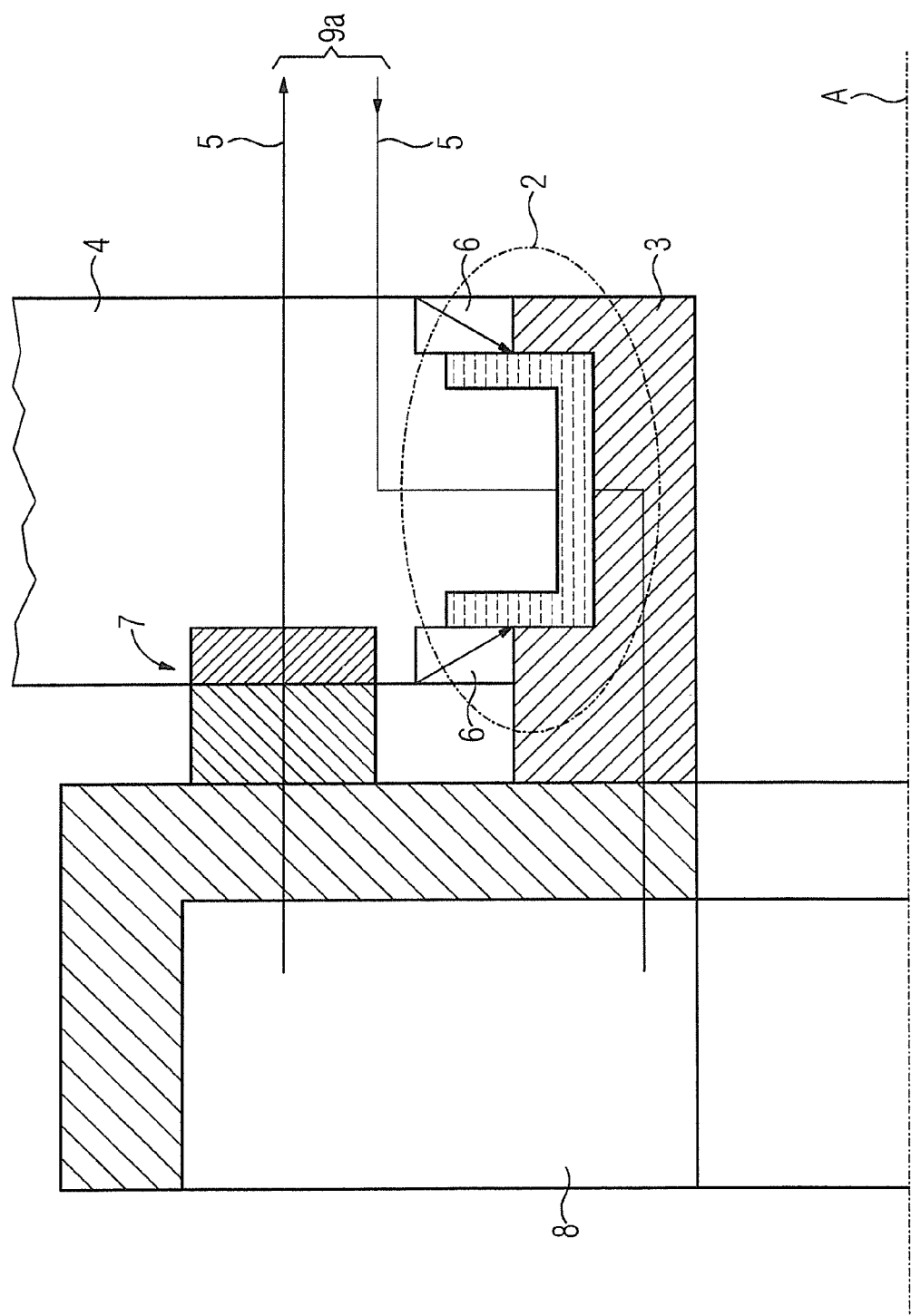

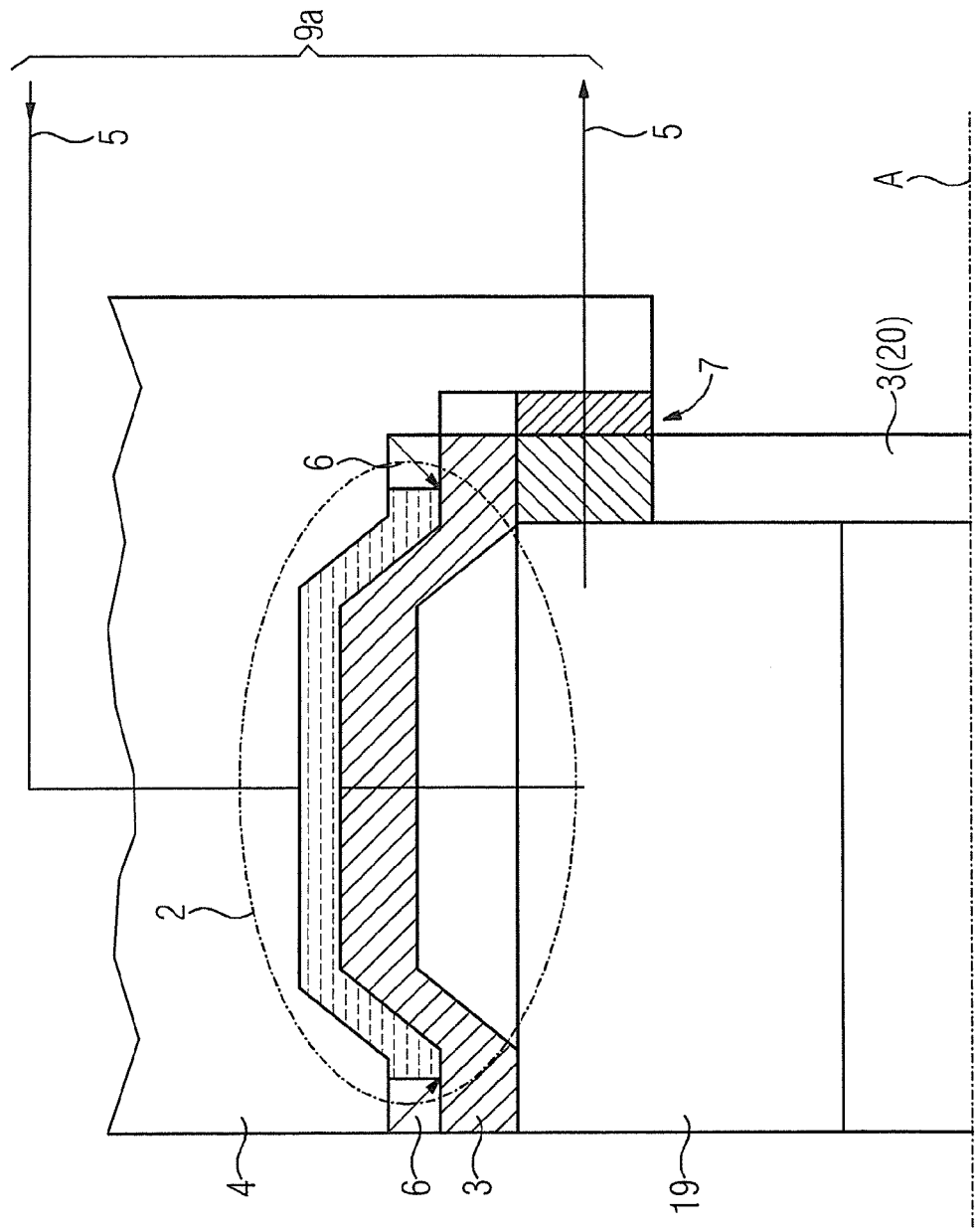

ROTATING UNIT OF A MEDICAL IMAGING DEVICE WITH A HYDROSTATIC SLIDE BEARING AND AN INTEGRATED COOLANT CONDUIT

BACKGROUND OF THE INVENTION

1. Field of the Invention

The invention concerns a rotating unit of a medical imaging device (in particular a computed tomography apparatus) with a hydrostatic slide bearing and an integrated coolant conduit. Furthermore, the invention concerns a medical imaging device (in particular a computer tomography apparatus) with such a rotating unit.

2. Description of the Prior Art

Computed tomography is a diagnostic method that is widely used in medical engineering. In such a method, a region of a patient or subject that is to be examined is exposed slice-by-slice with radiation, and exposures of the region of the subject or patient that is to be examined are acquired from various directions. An image reconstruction from the acquired exposures subsequently enables a two-dimensional or three-dimensional depiction of the examined region and contributes to the production of a diagnosis.

The computed tomography apparatuses that are used for this typically have a frame that has a stationary part and a part that can be tilted as necessary. The frame has at least one stationary part and is designed as a supporting structure of a rotatable part of the computed tomography apparatus. The rotating part has an acquisition system that includes at least one detector and at least one radiation source. The stationary part thereby forms a stator and the rotatable part forms a rotor. The rotor is borne in the stator by a bearing so that it may rotate, and the two parts form a rotating unit. The rotating part of the computed tomography apparatus has an essentially annular or cylindrical shape with a continuous central opening or a tunnel, and can be rotated around the axis of symmetry of this opening or of this tunnel. The radiation source and the detector thereby define a measurement region in which a subject or patient can be positioned so as to be movable. The detector and the radiation source are typically situated on diametrically opposite sides of the central opening. The detector thereby rotates with the radiation source around the rotation axis of the rotating part along which the subject or the patient is moved. Between the frame (thus the stationary part) and the rotatable part, a rotation bearing is formed that enables the rotation of the rotatable part relative to the stationary part. It is additionally possible that the entire rotating unit, composed of at least the rotation bearing, the rotor and stator, is designed so as to be able to tilt.

Computed tomography examinations require a very precise arrangement of the entire medical apparatus (in particular of the at least one acquisition system), which is directly linked with the image quality. Modern computed tomography apparatuses presently also have rotation speeds of up to approximately 240 $min^{-1}$ (revolutions per minute). Higher rotation speeds are also conceivable in the future, for example in the range of up to 400 $min^{-1}$.

Therefore, high mechanical demands are placed on such medical devices. Conventional, rotating units predominantly have a roller bearing in different embodiments (for example a ball bearing) between the rotor and the stator, wherein the rotation of the rotor is driven by a drive bearing or a direct drive, for example.

However, such a roller bearing is subject to a wear and must be serviced regularly (in particular be re-lubricated), which means a high service cost. Due to the wear, such a roller bearing has a limited lifespan. Moreover, a large amount of heat energy is released (in particular from the radiation source) during the operation of a computed tomography apparatus, which can likewise negatively affect the lifespan of such bearings by changing the contact pressure due to the thermal conductivity and the material expansion. Such rotation bearings are also sensitive to dust particles that if they reach the bearing surface, destroy the track of the roller body and additionally reduce the lifespan of the bearing. Such bearings are also sensitive to shocks or vibrations, such that the bearings must accordingly be protected (in particular during transport) with complicated protective measures. Moreover, the noise level of such bearings increases drastically with increasing rotation speed, so measures having high production and installation costs are required in order to bring the noise level to a level that is not disruptive, in particular for the patient and/or for the operating personnel.

SUMMARY OF THE INVENTION

An object of the invention is to address these problems and to provide a rotating unit for a medical imaging device with a stator and a rotor, in particular for a computed tomography apparatus, which can be operated more robustly, quieter, with a longer service life and with lower production, installation and service costs.

According to the invention, the rotating unit has at least one stator, at least one rotor that is rotatable relative to the stator, at least a portion of a circulation system for the circulation of a bearing medium, and at least one at least single-channel rotary joint (rotary feedthrough) situated between the rotor and the stator. The rotor is thereby borne (supported) by the bearing medium so as to be hydrostatically floating relative to the stator. The at least one portion of the circulation system for the circulation of the bearing medium has at least one opening situated at the stator and one opening situated at the rotor. These openings are open to (in fluid communication with) the hydrostatic bearing and to the rotary joint. The at least one portion of the circulation system is designed such that the bearing medium can be supplied (preferably under pressure) through the stator-side opening into the hydrostatic slide bearing and can be fed again through the rotor-side opening (as well as through the rotary joint) into the circulation system. Flow of the bearing medium from the stator-side opening of the slide bearing through the rotor-side opening and the rotary joint is thereby enabled. Thus a hydrostatic slide bearing of the rotation bearing is enabled between rotor and stator, as well as a cooling of the rotating unit (in particular of the rotor) by the bearing medium flow.

With such a circulation system, a hydrostatic slide bearing is achieved between the rotor and the stator, while a monitored and monitorable flow of the bearing medium through the hydrostatic slide bearing also is enabled. The flow of the bearing medium through the hydrostatic slide bearing additionally enables a cooling of the medical rotating unit according to the invention. In particular, a cooling of the rotor and of the stator as well as a passive cooling of the components attached to the rotor or to the stator is thereby enabled via thermal conduction. The monitored flow of the bearing medium between the rotor and the stator in operation of the medical device (preferably of the computed tomography apparatus) enables that the heat released by the medical imaging device and/or by the rotating unit is discharged at least in part to the bearing medium via the contact of the bearing medium with the surface of the rotor, and with the surface of the stator and with the additional surfaces of the circulation system. Thermal energy can be transported away from the rotation bearing via the direction of the bearing medium through the hydrostatic slide bearing by means of the circulation system. The cooling at the rotating part of the medical imaging device (in particular the computed tomography apparatus) can thereby be designed to be smaller, whereby costs and most of all space are saved.

The bearing medium that is used is a fluid, for example oil or gas. Oil—in particular a mineral oil or a synthetic oil or a mixture of these—is advantageously used as a bearing medium. In comparison to an air bearing, among other things a hydrostatic bearing with a fluid bearing medium has the advantage of having better damping properties. The necessity of using control devices to suppress vibrations (in particular of an unbalanced rotor) is thereby omitted. This is particularly advantageous in computed tomography apparatuses that have rotors that are heavy and severely out of balance, which rotors support at least one acquisition system that should rotated as centrally as possible in order to ensure a good image quality. Furthermore, fluids (for example oil) have a much higher viscosity than air. While only a very thin bearing gap can be generated given an air bearing, a hydrostatic bearing with a fluid (for example oil) enables the generation of a larger bearing gap. This in turn enables a greater flow of the fluid through the rotation bearing, allowing the rotation bearing to be simpler to cool. The bearing medium can also be a gas or a gas mixture. The bearing medium can include additives or additional compounds, whereby the physical properties of the bearing medium (such as lubricity, viscosity, temperature and/or chemical stability, pressure and/or temperature response) are affected. Alternatively, gas is used as a bearing medium. The gas is advantageously provided from an external pressurized gas supply (for example a gas cylinder). In this case, the gas is pushed through the at least one inlet opening into the rotation bearing between rotor and stator and can leave the rotation bearing through the at least one outlet opening. For example, the escaping gas is fed into the external pressurized gas supply again by means of a compression unit or a condenser and/or is stored in an additional pressurized container for later use.

The rotor and the stator are designed such that, in operation, they form a hydrostatic slide bearing together with the bearing medium. A hydrostatic slide bearing is characterized in that a bearing medium is actively pressed in between the rotor and the stator through at least one inlet opening of said stator, such that the rotor surface and stator surface are separated from one another by a thin bearing medium film. In the following, the volume between the rotor and the stator is designated as a bearing gap. The bearing medium is advantageously directed or pushed at high pressure between the rotor and the stator. As a result of this, the rotation bearing of such a rotation unit has nearly no contact pressure, such that a wear of the bearing is practically nonexistent. In that rotor and stator are not in direct contact with one another, they are barely subject to friction or wear, such that the lifespan of the rotation bearing and the rotating unit are increased overall. Via the hydrostatic slide bearing of the rotor relative to the stator, a rotation bearing—and in turn a rotating unit—are thus provided which has or, respectively, have a very low wear and require(s) little maintenance. Moreover, such a rotating unit according to the invention has a lower coefficient of friction, whereby the rotation drive of the rotating unit according to the invention is significantly reduced, such that the drive motors can be dimensioned smaller or faster rotation speeds can be achieved, for example.

In addition, the rotor has at least one outlet opening whereby the bearing medium can be actively directed through into the bearing gap so that an active lubrication of the bearing by the bearing medium takes place. The active lubrication or direction of the bearing medium occurs by means of the circulation system which is designed for the circulation of the bearing medium (preferably under pressure). The circulation system additionally comprises at least a first part which is part of the rotating unit and the [sic] the bearing gap; at least one inlet opening penetrating through the bearing gap and preferably arranged at the rotor; at least one outlet opening penetrating through the bearing gap and preferably arranged at the rotor; and an advantageously single-channel rotary joint arranged between the rotor and the stator, which rotary joint is connected with at least one outlet opening penetrating through the bearing gap and preferably arranged at the rotor. The preferably single-channel rotary joint is advantageously connected with the rotor-side opening by means of at least one conduit. This at least one conduit advantageously extends on the rotating part, thus on the rotor and/or on components which are connected to the rotor. The rotary joint is advantageously connected with the hydrostatic slide bearing via the rotor-side opening such that the bearing medium can flow back from the hydrostatic slide bearing into the circulation system in a controlled manner. A bearing medium flow from the stationary part to the rotating part of the rotating unit is thereby achieved via the hydrostatic slide bearing and the rotary joint, which enables a very large cooling effect due to the uninterrupted bearing medium flow. The bearing medium (which is simultaneously used as a coolant in this context) arrives from the stationary part to the rotating part of the rotating unit via the hydrostatic slide bearing, and there it can be specifically directed (advantageously by means of at least one conduit) along defined components, for example, in order to actively cool these. This is particularly advantageous given a computed tomography apparatus in which the radiation source arranged at the stator generates the most heat. The cooling capacity can additionally be affected via the adjustment of the flow rate. The number of cooling pauses of the rotating unit thus can be reduced, or a cooling pause can be superfluous. This is particularly advantageous given a computed tomography apparatus in which the radiation source arranged at the stator has properties which are strongly temperature-dependent. In addition to this, the necessity of using a second rotary joint is dispelled via this arrangement since the hydrostatic slide bearing is, so to speak, used as a rotary joint for the bearing medium in one direction of the circulation system. This also enables a compact structural design and a cost savings. Furthermore, with this arrangement only a single preparation is necessary for a medium that is simultaneously used as a coolant and bearing medium. A compact structural design on the one hand and a cost savings are likewise achieved.

The circulation system is located at least in part at the rotating unit and/or at least in part outside of the rotating unit. The first part of the circulation system—which is part of the rotating unit—includes the bearing gap between the rotor and the stator, the rotary joint, the openings penetrating through to the bearing gap, and possibly at least one conduit arranged at the rotor. The circulation system furthermore advantageously has an additional part that is preferably fashioned at the stator or outside of the stator, for example outside of the rotating unit, and is designed to circulate the bearing medium (preferably under pressure). The additional part can be a pressure generation unit and is connected with the first part (for example via a connector). The additional part of the circulation system is advantageously connected with this first part, wherein the connection between the first part and the additional part is realized via a connector, for example.

In particular, the rotor and the stator are designed and arranged such that, in operation of the rotating unit, the bearing medium flowing between the rotor and the rotor is enclosed in an annular gap and essentially can only enter and exit the rotation bearing through the inlet and outlet openings provided for this. For this purpose, the rotating unit has at least one sealing arrangement that seals the volume in which the bearing medium is directed between the rotor and the stator. The rotating unit also has at least one additional sealing arrangement that likewise seals the rotary joint. For example, such a sealing element or sealing arrangement includes at least one annular seal that is attached or arranged on the facing sides of the rotor and/or the stator. Such a sealing element or sealing arrangement is designed such that essentially no bearing medium can escape through the sealing element or sealing arrangement, even given rotation of the rotor. Furthermore, such a sealing element or sealing arrangement is designed such that the entrance of contaminants from the environment into the rotation bearing is essentially prevented. The sealing function of such a sealing element or sealing arrangement is supported by a corresponding shaping of the stator and/or of the rotor, in particular their facing sides. Such a sealing element or sealing arrangement is fashioned such that it retains or improves its sealing function both at high rotation speeds of the rotor and at high pressure of the bearing medium and/or given high (for example thermal or mechanical) loading of the rotating unit. A rotating unit according to the invention with such a rotation bearing therefore has the advantage that it is operable without excessively cleaner processes, without complicated labyrinth seals and even in non-optimal environmental conditions (for example in a dirty environment). A rotation bearing is thereby achieved that is insensitive to dust particles. It is difficult for external dust to penetrate into the rotation bearing due to the sealed bearing medium flowing through between the rotor and the stator. Furthermore, a lubrication of the rotation bearing is not necessary, such that fewer or less frequent service measures must be executed. Moreover, the service measures are simplified, such that less time is claimed for these, whereby there is a cost savings. A robust rotating unit is thus achieved.

Furthermore, during the operation of the bearing or of the rotating unit, even at high rotation speeds, a significant reduction of the noise level is achieved because roller body noises are not present. The stress of a patient undergoing an examination with such a medical device, in particular with such a computed tomography apparatus, can thereby be significantly reduced, which entails a win both for patients and for the personnel. Furthermore, additional noise reduction measures are also not needed, so the costs and the production and installation complexity of such a rotating unit or, respectively, of a imaging device with such a rotating unit are reduced.

Moreover, a rotating unit with such a rotation bearing—and thus an imaging device with such a rotating unit—is significantly less sensitive to shocks and/or vibrations, whereby the transport of such devices becomes simpler, faster and more cost-effective, for example.

Finally, due to the hydrostatic slide bearing via the bearing medium such a rotating unit has very good damping properties, which is in particular advantageous in a computed tomography apparatus with high rotation speeds and heavy rotating components.

Overall, a very compact, nearly noiseless and robust rotating unit is thereby provided.

In an embodiment of the rotating unit, at least the rotor-side part of the circulation system of the rotating unit (thus the part of the circulation system of the rotating unit that is arranged at the rotor) has at least one (preferably adjustable) choke valve. This allows possibility monitoring (advantageously to decrease) the pressure of the bearing medium in the rotor-side part of the circulation system. The flow of the bearing medium in the circulation system can thereby additionally be affected.

In a further embodiment of the rotating unit according to the invention, at least the rotor-side part of the circulation system of the rotating unit (thus the part of the circulation system of the rotating unit that is arranged at the rotor) has at least one distributor to distribute the bearing medium in different conduits. This causes the bearing medium coming from the hydrostatic bearing to be directed into different conduits at the rotor. At least one of these conduits has at least one (preferably adjustable) choke valve, so the pressure or the flow rate in this conduit can be controlled. Multiple conduits can each have at least one (preferably adjustable) choke valve, so the pressure or the flow rate in the different conduits can be chosen differently.

A further development of the rotating unit according to the invention provides that the circulation system has means to circulate the bearing medium, for example one or more pumps and/or one or more compressors so that bearing medium can be supplied into the bearing gap between the rotor and the stator (preferably under pressure) through the at least one inlet opening. The circulation of the bearing medium is therefore enabled. The first part of the circulation system has one or more units to circulate the bearing medium, for example one or more pumps and/or one or more compressors. This enables the circulation of the bearing medium in the rotor-side part and the regulation of the flow rate and the return feed into the further part of the circulation system. The circulation system or the first and/or the additional portion of this circulation system advantageously have additional elements with which the flow rate, the temperature and/or the pressure of the bearing medium can be measured and/or modified. For example, such elements are valves, pressure measurement devices, temperature measurement devices and/or flow measurement devices. These elements are advantageously arranged at the stator or outside of the stator, for example outside of the rotating unit. In addition, the flow of the bearing medium can be affected by the adjustment of the pump and/or compressor capacity. In this context, additional devices such as return valves and/or choke valves are used. A controlled and controllable flow of the bearing medium is thereby enabled. The circulation system is also advantageously designed to be closed and/or sealed and/or at least partially pressure-resistant.

In an embodiment of the present invention, the rotor-side part of the circulation system has at least one conduit which is arranged at the rotor and/or at a component arranged at the rotor. This achieves a direct cooling of the rotor or the components that are arranged at the rotor via the guidance of the conduit (for example along them). Heat can thereby be specifically transported away from a defined location of the rotor or from a defined component. The rotor-side part of the circulation system can have multiple conduits that are arranged at the rotor and/or at different components of the rotor.

In another embodiment of the rotating unit according to the invention, at least a portion of the bearing medium of the at least one rotor-side part of the circulation system is designated for cooling and bearing a radiation source of an x-ray radiator. A very large cooling effect of the radiation source is thereby enabled since the bearing medium (here also as a coolant) can flow uninterrupted through the radiation source. The cooling effect or cooling capacity can additionally be adjusted by adjusting the flow rate of the bearing medium.

Cooling pauses of the radiation source thus can be prevented, so longer scan times can be achieved, which means an improved customer usage. In addition, the active cooling components at the rotor-side part can be dimensioned smaller or even be completely omitted. This means an enormous space savings on the rotor side. Other components can be attached to the rotor side, allowing additional examination modes to be enabled, for example. Moreover, fewer components on the rotor side means a smaller moment of inertia of the rotor, so the rotation drive can likewise be dimensioned smaller.

Particles that form due to the wear of the sealing arrangement and/or of the sealing element or due to the time-dependent degradation of the surface of the rotor and/or of the stator, or that have been introduced during assembly or that nevertheless arrive in the rotation bearing in spite of the sealing means, can simply be eliminated by changing the bearing medium, or by a filtering of the bearing medium. Service measures of the rotating unit according to the invention therefore essentially consist of filtering and/or exchanging the bearing medium.

In another embodiment of the rotating unit according to the invention, the circulation system has at least one filter to filter the bearing medium. This is particularly advantageous because the radiation beam radiates through the bearing medium. The presence of particles in the bearing of the radiation source would therefore lead to image artifacts or, respectively, to a degraded image quality. The filter is preferably attached to the stator-side part or to a part of the circulation system that is located outside of the stator or the rotating unit. Space at the rotor is thereby saved, and an exchange of the filter is simplified. Alternatively or additionally, at least one conduit of the circulation system that is mounted at the rotor has such a filter. This ensures that no particles can arrive in the bearing of the radiation source. This is particularly advantageous because the radiation beam radiates through the bearing medium. The presence of particles in the bearing of the radiation source would therefore lead to image artifacts or to a degraded image quality [sic; these previous two lines are a direct copy from earlier in this same paragraph]. The bearing medium can thereby be permanently cleaned of dust particles that are possibly present, whereby maintenance measures are further simplified and must be implemented less often. This measure additionally increases the lifespan of the rotation bearing because a possible wear is even further reduced or, respectively, prevented.

In another embodiment of the rotating unit according to the invention, the circulation system has at least one connector for an external cooler to cool the bearing medium. Overall, this additional measure enables an improvement of the cooling of the rotating unit or of the rotation bearing that is due to the flow of the bearing medium. More heat energy can thereby be transported away from the rotation bearing. The cooling of the rotation bearing—and thus of the rotating unit—is thus more efficient. The cooling capacity thus can be adapted simply to the cooling task. For example, the cooling capacity can be increased if the radiation source is operated. Cooling pauses of the radiation source or of the rotating unit can thereby be prevented. The external cooler is preferably connected with the circulation system at a part of said circulation system which is located at the stator or outside of the stator, and is itself located at the stator or outside of the stator or the rotating unit, such that space on the rotor is saved. This additionally enables a better passive cooling of the components arranged on the rotating part of a medical device. The cooling at the rotor can thereby be of smaller design, so higher capacities can be achieved. These measures in particular enable longer scan times and thus an improved customer use, for a computed tomography apparatus. With suitably designed cooling by the cooler, the entire cooling at the rotor can be foregone, so maximum space is saved and a smaller drive is required.

Alternatively or additionally, in a further embodiment of the rotating unit according to the invention, the circulation system has a cooler to cool the bearing medium. The cooler is advantageously integrated into the circulation system. An additional development of the rotating unit according to the invention according to this embodiment provides that the cooler has at least one heat exchanger to cool the bearing medium and is arranged either in or outside of the stator of the rotating unit. The cooler is preferably arranged in a part of the circulation system which is located at the stator or outside of the stator or, respectively, the rotating unit, such that space on the rotor can be saved. This measure moreover has the same advantages as the external cooler discussed in the preceding. An additional advantage in connection with an external cooler is that possible leakiness at the connection points is thereby prevented.

Such an external or integrated cooler can have at least one heat exchanger, preferably a spiral-shaped heat exchanger. This heat exchanger is preferably arranged at the stator or outside of the stator or the rotating unit. An even better cooling effect of the medical imaging device (in particular of the computed tomography apparatus) is enabled via an external or internal cooler which is integrated into the circulation system of the bearing medium. Higher capacities of the radiation source can be maintained for longer, whereby the scan time can be chosen to be longer, whereby numerous examination modes are enabled, which means a higher customer usage.

Furthermore, the invention concerns a medical imaging device with a rotating unit according to the invention. The medical imaging device is in particular a computed tomography apparatus with such a rotating unit. This is particularly advantageous because a computed tomography apparatus (namely the at least one radiation source thereof) releases a large amount of thermal energy, which alters the radiation geometry of the acquisition system, which negatively affects the image quality. A computed tomography apparatus with a rotating unit according to the invention has the additional advantage that at least a portion of the heat released by the radiation source is specifically transported away by the flow of at least a portion of the bearing medium, so the image quality is improved. In the medical device, in particular a computed tomography apparatus, with a rotating unit according to the invention, the rotating unit is designed so that it can be tilted relative to the medical imaging device, in particular relative to the stationary part of the medical imaging device.

The advantages cited for the rotating unit also apply to the medical imaging device.

BRIEF DESCRIPTION OF THE DRAWINGS

FIG. 1 is a schematic sectional presentation of a computed tomography apparatus with a hydrostatic slide bearing between a rotating part of the computed tomography part, the rotating part having an acquisition system, and a stationary part of the computed tomography part, FIG. 2 is a detailed, schematic sectional presentation of a portion of a rotating unit according to the invention of a computed tomography apparatus, with a hydrostatic slide bearing between a rotating part of the computed tomography apparatus, that has at least one component and a stationary part of said computed tomography apparatus.

FIG. 3 is a further detailed, schematic sectional presentation of a portion of a rotating unit according to the invention of a computed tomography apparatus, with a hydrostatic slide bearing between a rotating part of the computed tomography apparatus having a radiation source and a stationary part of said computed tomography apparatus.

DESCRIPTION OF THE PREFERRED EMBODIMENTS

FIG. 1 shows a schematic drawing in sectional presentation of a computed tomography apparatus 1 having a rotating unit with a hydrostatic slide bearing 2 between a rotating part having at least one component (for example an acquisition system) 8 and a rotor 3 and a stationary part forming a stator. The rotating part and stationary part belong to the computed tomography apparatus 1. The rotating part is thereby borne, hydrostatically floating, by a bearing medium 5 relative to the stationary part of the computed tomography apparatus 1 such that the rotating part is rotatable around the rotation axis (A). Furthermore, the surfaces of the rotor 3 and of the stator 4 facing toward the bearing medium 5 are designed to be rotationally symmetrical. The bearing medium 5 is also introduced at high pressure between the rotor 3 and the stator 4 such that a bearing gap arises between rotor 3 and stator 4, in which bearing gap the bearing medium 5 is sealed tight at the facing sides of the rotation bearing by a suitable sealing arrangement 6. The bearing medium 5 can thus essentially escape from and be supplied only from the openings provided for this, which openings are connected with the circulation system. The surfaces of the rotor 3 and of the stator 4 that face towards the bearing medium 5 thereby have no contact in operation. Preferably annular sealing elements 6 are provided on the sides of the rotor 3 to laterally seal the bearing gap. For example, such sealing elements 6 comprise O-ring seals, for example with a square profile in cross section. The sealing elements 6 are advantageously fashioned such that they have or improve a sealing function given overpressure and/or underpressure of the bearing medium 5 in the circulation system. In this example, the stator 4 additionally has at least two openings penetrating through to the bearing gap, which openings are part of the circulation system at the rotating unit and enable a flow of the bearing medium 5 from hydrostatic slide bearing 2 through the rotor 3, across the rotary joint 7 and back into the circulation system 9, 9b. The circulation system 9 comprises a first part 9a and an additional part 9b. The first part of the circulation system 9a is part of the rotating unit and is connected with the additional part of the circulation system 9b. The first part of the circulation system 9a in this example comprises: an opening arranged at the stator, through which opening the bearing medium 5 is supplied into the hydrostatic slide bearing 2 (preferably under pressure); an opening arranged at the rotor, through which opening the bearing medium 5 located in the hydrostatic slide bearing 2 is conducted on the rotor; multiple conduits 10 which extend along the acquisition system or at least one rotor component 8 of the rotating unit and that are connected with a rotary joint such that the bearing medium 5 is directed back again into the circulation system 9, 9b. A conduit 10 thereby has a pump 14a, and an additional conduit 10 arranged in parallel with this has a choke valve 12. The first part of the circulation system 9a possibly has a pressure measurement device 13. The additional part 9b of the circulation system 9 possibly has a cooler 11, a pump 14b, a filter 15, a flow measurement device 16, a temperature measurement device 17 and a bearing medium tank 19. Heat can thereby be transported away (in particular from the rotor 3) effectively and in a targeted manner, both as concerns the capacity and as concerns the location of the rotating unit. The rotor 3 with the components 8 attached to the rotor can be rotated on the rotation axis (A) around the stator (4).

FIG. 2 shows a detailed schematic section presentation of a part of a rotating unit according to the invention of a computed tomography apparatus 1 with a hydrostatic slide bearing 2 between a rotating part having at least one component 8 and a stationary part of the computed tomography apparatus 1. The rotating unit has a stator 4 and a rotor 3 which are borne so as to be hydrostatically floating 2 via the bearing medium 5. The surfaces of the rotor 3 and of the stator 4 that are facing toward the bearing medium 5 are fashioned such that said rotor is rotatable around the stator 4, thus is rotationally symmetrical. The bearing medium 5 is directed through the hydrostatic slide bearing 2 through an opening arranged at the stator 4. The bearing medium 5 is directed further on the rotor 3 through an opening arranged at said rotor 3. In this shown example, a frame that is L-shaped in cross section is arranged on the rotor 3, on which frame is in turn arranged at least one component 8 (for example a part of an acquisition system). Conduits (not shown) are directed through the rotor 3 and through and/or along the at least one component 8 so that heat is absorbed from the at least one component by the bearing medium flow. The bearing medium is subsequently directed again through the rotary joint to the stator 4 and supplied to the additional part of the circulation system 9b. In this example, the surface of the rotor 3 that faces toward the bearing medium in the hydrostatic slide bearing has a U-shaped cross section. In addition to this, the rotary joint 7 is designed to be annular and mounted between frame and stator 4.

As noted above, FIG. 1 is a schematic sectional presentation of a computed tomography apparatus 1 having a rotating unit with a hydrostatic slide bearing 2 between a rotating part having an acquisition system 7, the rotating part having a rotor 3, and a stationary part having at least one stator 4 of the computed tomography apparatus 1, as well as a circulation system 8 that includes a cooling system 9 for the circulation of the bearing medium 5 between the rotor 3 and the stator 4, thus through the bearing gap present in operation. The cooling system 8 cools a bearing medium 5 coming from the hydrostatic slide bearing. The rotating part has an acquisition system 7 with multiple components, namely at least one radiation source and a detector. In this example, the components are arranged on a frame with an L-shaped cross section. The rotating part is borne such that it can rotate around the axis (A). The rotation of the rotating part is driven by a drive (not shown). In operation, rotor 3 and stator 4 form a hydrostatic slide bearing 2 with the bearing medium 5 flowing through the bearing gap. The acquisition system 7 is in thermal contact with the frame of the rotating part. In addition to this, the frame is likewise in thermal contact with the rotor 3 via the contact surfaces 10. A passive heat transport is thereby present between the components of the rotating part (in particular of the acquisition system 7) via the frame and the rotor 3 via thermal conduction. This heat can be discharged at least in part to the bearing medium 5 via the contact surface of the rotor 3 with the bearing medium 5 in the bearing gap. Furthermore, the stator 4 of the rotating unit has at least two openings penetrating through to the bearing gap between rotor 3 and stator 4. These openings are connected with the bearing gap (which is otherwise designed to be sealed) and with a stator-side part of a circulation system 8 for the circulation of the bearing medium 5. The circulation system 8 thereby comprises at least: the bearing gap present between rotor 3 and stator 4 in operation; the at least two inlet and outlet openings penetrating through to the bearing gap; and a stator-side part that is arranged at the stator of the rotating unit or is arranged outside of the rotating unit, advantageously at the stationary part, or can be arranged there. Furthermore, the stator-side part of the circulation system 8 comprises at least one external or integrated cooling system 9 with at least one cooler unit to cool the bearing medium 5. The stator-side part of the cooling system 8 advantageously additionally has a bearing medium tank 11; a pump 12 to circulate the bearing medium 5 in the circulation system; a filter 13 to filter the bearing medium 5; and/or diverse measurement and/or control devices 14, for example pressure, temperature and/or flow measurement devices. The circulation system 8 is designed such that a circulation of the bearing medium 5 through said circulation system 8 takes place. Heat energy is thereby effectively transported away via the bearing medium 5 from the rotating part of the rotating unit or, respectively, of the computed tomography apparatus 1 (in particular from the components 7 of the rotating part). An effective passive cooling takes place, in particular of the rotating part of the rotating unit of the computed tomography apparatus 1. In particular, the components of the acquisition system 7 of the rotating part can be passively cooled.

FIG. 3 shows a detailed schematic section presentation of a part of a rotating unit according to the invention of a computed tomography apparatus 1 with a hydrostatic slide bearing 2 between a rotating part having at least one component 8 and a stationary part of the computed tomography apparatus 1. The rotating unit has a stator 4 and a rotor 3 which are borne so as to be hydrostatically floating 2 via the bearing medium 5. The cross section of the surfaces of the rotor 3 and of the stator 4 that are facing toward one another are thereby complementary in the direction of the rotation axis A of the rotating unit. The bearing medium 5 is directed through the hydrostatic slide bearing 2 through an opening arranged at the stator 4. The bearing medium 5 is directed further on the rotor 3 through an opening arranged at said rotor 3. In this shown example, a radiation source 19 is arranged at the rotor 3. At least one conduit (not additionally shown) is in connection with the bearing of the radiation source so that at least a portion of the bearing medium from the hydrostatic slide bearing 2 is used for the bearing and is additionally used for cooling said radiation source 19 via the flow of the bearing medium 5 through the bearing of said radiation source 19. Heat is thereby specifically and directly absorbed from the radiation source by the bearing medium flow and is subsequently supplied again to the stator 4 or into the additional part of the circulation system 9b via the return feed of the bearing medium 5 through the rotary joint. In this example, the surface of the rotor 3 that faces towards the bearing medium in the hydrostatic slide bearing has a hat-shaped cross section which additionally improves the stability in the direction of the rotation axis (A), which is particularly advantageous in the case of a rotating unit (of a computed tomography apparatus, for example) that can be tilted. In addition to this, the rotary joint 7 is designed to be annular and, depending on embodiment, is arranged between rotor 3 and stator 4 or between stator 4 and a module 20 arranged on the rotor.

Although modifications and changes may be suggested by those skilled in the art, it is the intention of the inventor to embody within the patent warranted hereon all changes and modifications as reasonably and properly come within the scope of his contribution to the art.

I claim as my invention:

1. A rotating unit of a medical imaging apparatus, comprising:

a stator;

a rotor mounted for rotation relative to said stator;

a portion of a circulation system that circulates a bearing medium in a gap between said stator and said rotor in which said rotor hydrostatically floats so as to be rotatable relative to said stator;

a single-channel rotary joint between said rotor and said stator;

said portion of said circulation system comprising a stator-side opening and a rotor-side opening in fluid communication with said bearing medium and said rotary joint, said portion of said circulation system being configured to cause said bearing medium to be supplied through said stator-side opening into said gap and to be supplied from said rotor-side opening and said rotary joint into a remainder of said circulation system, allowing said bearing medium to flow through said portion of said circulation system.

2. A rotating unit as claimed in claim 1 wherein said portion of said circulation system comprises a choke valve situated in proximity to said rotor-side opening.

3. A rotating unit as claimed in claim 1 wherein said portion of said circulation system comprises a distributor in proximity to said rotor-side opening that distributes said bearing medium in respectively different conduits.

4. A rotating unit as claimed in claim 1 wherein said portion of said circulation system comprises at least one unit that imparts a flow to said bearing medium, selected from the group consisting of compressors and pumps, situated in proximity to said rotor-side opening.

5. A rotating unit as claimed in claim 1 wherein said portion of said circulation system comprises at least one conduit for said bearing medium in proximity to said rotor-side opening.

6. A rotating unit as claimed in claim 5 comprising a component that participates in generating image data, mounted to said rotor, and wherein said at least one conduit proceeds in or around said at least one component.

7. A rotating unit as claimed in claim 6 wherein said component is an x-ray source, and wherein said bearing medium in said conduit is in thermal communication with said x-ray source and removes heat from said x-ray source that is generated by said x-ray source during operation thereof.

8. A rotating unit as claimed in claim 1 comprising an x-ray source mounted at said rotor, and wherein said bearing medium is in thermal communication with said x-ray source and removes heat from said x-ray source that is generated by said x-ray source during operation thereof.

9. A rotating unit as claimed in claim 1 wherein said portion of said circulation system comprises at least one filter that filters said bearing medium.

10. A medical imaging apparatus comprising:

a stator;

a rotor mounted for rotation relative to said stator;

a circulation system that circulates a bearing medium in a gap between said stator and said rotor in which said rotor hydrostatically floats so as to be rotatable relative to said stator, with a portion of said circulation system being situated on said rotor;

a single-channel rotary joint between said rotor and said stator;

said portion of said circulation system comprising a stator-side opening and a rotor-side opening in fluid communication with said bearing medium and said rotary joint, said portion of said circulation system being configured to cause said bearing medium to be supplied through said stator-side opening into said gap and to be supplied from said rotor-side opening and said rotary joint into a remainder of said circulation system, allowing said bearing medium to flow through said portion of said circulation system.

11. A medical imaging apparatus as claimed in claim 10 wherein said portion of said circulation system comprises a choke valve situated in proximity to said rotor-side opening.

12. A medical imaging apparatus as claimed in claim 10 wherein said portion of said circulation system comprises a distributor in proximity to said rotor-side opening that distributes said bearing medium in that respectively different conduits.

13. A medical imaging device as claimed in claim 10 wherein said portion of said circulation system comprises at least one unit that in parts a flow to said bearing medium, selected from the group consisting of compressors and pumps, situated in proximity to said rotor-side opening.

14. A medical imaging apparatus as claimed in claim 10 wherein said portion of said circulation system comprises at least one conduit for said bearing medium in proximity to said rotor-side opening.

15. A medical imaging apparatus as claimed in claim 14 comprising a component that participates in generating image data, mounted to said rotor, and wherein said at least one conduit proceeds in or around said at least one component.

16. A medical imaging apparatus as claimed in claim 15 wherein said component is an x-ray source, and wherein said bearing medium in said conduit is in thermal communication with said x-ray source and removes heat from said x-ray source that is generated by said x-ray source during operation thereof.

17. A medical imaging apparatus as claimed in claim 10 comprising an x-ray source mounted at said rotor, and a radiation detector, said x-ray source and said radiation detector being configured to generate computed tomography data of a subject situated therebetween in a central opening of said rotor, and wherein said bearing medium is in thermal communication with said x-ray source and removes heat from said x-ray source that is generated by said x-ray source during operation thereof.

18. A medical imaging apparatus as claimed in claim 10 wherein said portion of said circulation system comprises at least one filter that filters said bearing medium.

19. A medical imaging apparatus as claimed in claim 10 wherein said circulation system comprises a connection to an external cooler that is external to said circulation system.

20. A medical imaging apparatus as claimed in claim 10 wherein said circulation system comprises a cooler that cools said bearing medium.

* * * * *